United States Patent [19]

Nishiyama et al.

[11] 4,218,237
[45] Aug. 19, 1980

[54] PYRIDINE-2-THIO, -2-SULFINYL, AND -2-SULFONYL SULFONANILIDE COMPOUNDS USEFUL AS A HERBICIDAL COMPONENT

[75] Inventors: Ryuzo Nishiyama, Takatsuki; Kanichi Fujikawa, Kusatsu; Fumio Kimura, Kusatsu; Rikuo Nasu, Kusatsu; Nobuyuki Sakashita, Kusatsu; Shigeyuki Nishimura, Shiga, all of Japan

[73] Assignee: Ishihara Sangyo Kaisha Limited, Osaka, Japan

[21] Appl. No.: 961,518

[22] Filed: Nov. 17, 1978

[30] Foreign Application Priority Data

Nov. 29, 1977 [JP] Japan .................................. 52-143084
Mar. 29, 1978 [JP] Japan .................................. 53-36348

[51] Int. Cl.² ...................... C07D 213/70; A01N 9/22
[52] U.S. Cl. ............................................. 71/94; 71/103; 546/293; 546/295; 546/302; 546/303
[58] Field of Search ................... 546/295, 303, 293; 71/94, 103

[56] References Cited

U.S. PATENT DOCUMENTS

| | | | |
|---|---|---|---|
| 3,725,421 | 4/1973 | Domenico | 260/294.8 F |
| 3,977,861 | 8/1976 | Kawamura | 71/92 |
| 4,005,141 | 1/1977 | Moore | 260/556 F |
| 4,067,726 | 1/1978 | Sasse | 71/120 |

*Primary Examiner*—Donald G. Daus
*Assistant Examiner*—Lisa Jones
*Attorney, Agent, or Firm*—Oblon, Fisher, Spivak, McClelland & Maier

[57] ABSTRACT

A sulfonanilide compounds having the formula (I):

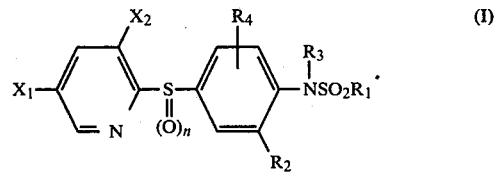

wherein $X_1$ is hydrogen atom, a halogen atom, methyl group or trifluoromethyl group, $X_2$ is hydrogen atom or a halogen atom, $R_1$ is a ($C_1$–$C_4$) alkyl group or a halo($C_1$–$C_4$) alkyl group, $R_2$ is hydrogen atom, a ($C_1$–$C_4$) alkyl group, trifluoromethyl group or nitro group, $R_3$ is hydrogen atom, —$SO_2R_1$ group ($R_1$ is the same as defined above), a ($C_2$–$C_4$) acyl group, a ($C_2$–$C_4$) acylmethyl group, a ($C_1$–$C_4$) alkyl group, a ($C_1$–$C_4$) alkoxy ($C_1$–$C_4$) alkyl group or a ($C_3$–$C_4$) alkenyl group, $R_4$ is hydrogen atom or a halogen atom, and n is an integer of 0 to 2; and a salt thereof, which is useful as a herbicidal component.

37 Claims, No Drawings

PYRIDINE-2-THIO, -2-SULFINYL, AND -2-SULFONYL SULFONANILIDE COMPOUNDS USEFUL AS A HERBICIDAL COMPONENT

BACKGROUND OF THE INVENTION

1. Field of the Invention

This invention relates to a novel compound useful as a herbicide for agriculture and horticulture, to a herbicidal composition containing the compound, to a method of controlling weeds using the same, and to a process for preparing the compound.

2. Description of the Prior Art

It has been known that phenyl substituted sulfonanilides have herbicidal effects in U.S. Pat. No. 4,005,141. However, any pyridyl substituted sulfonanilide has not been known.

The inventors have studied and found that certain pyridyl substituted sulfonanilides such as 4-(pyridine-2-ylthio) trifluoromethanesulfonanilide are useful as herbicides in an agricultural field for certain plants and have superior herbicidal effect in comparison with the compounds described in U.S. Pat. No. 4,005,141 especially for controlling cyperaceae weeds such as nutsedge (*Cyperus rotundus* L., *Cyperus esculentus* L.).

SUMMARY OF THE INVENTION

It is an object of the present invention to provide a novel sulfonanilide compound having the formula (I):

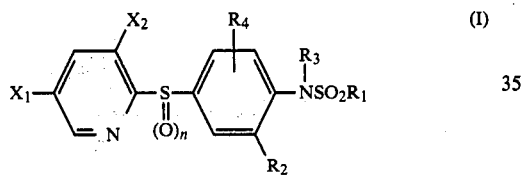

wherein $X_1$ is hydrogen atom, a halogen atom, methyl group or trifluoromethyl group, $X_2$ is hydrogen atom or a halogen atom, $R_1$ is a $(C_1-C_4)$ alkyl group or a halo $(C_1-C_4)$ alkyl group, $R_2$ is hydrogen atom, a $(C_1-C_4)$ alkyl group, trifluoromethyl group or nitro group, $R_3$ is hydrogen atom, $-SO_2R_1$ group ($R_1$ is the same as defined above), a $(C_2-C_4)$ acyl groups, a $(C_2-C_4)$ acylmethyl group, a $(C_1-C_4)$ alkyl group, a $(C_1-C_4)$ alkoxy $(C_1-C_4)$ alkyl group or a $(C_3-C_4)$ alkenyl group, $R_4$ is hydrogen atom or a halogen atom, and n is an integer of 0 to 2; and a salt thereof.

It is another object of the present invention to provide a herbicidal composition comprising a herbicidally effective amount of at least one compound of the formula (I) as an active ingredient and agriculturally acceptable adjuvants.

It is the other object of the present invention to provide a method for controlling weeds using the herbicidal composition.

It is also the other object of the present invention to provide a process for preparing novel sulfonanilide compounds.

DETAILED DESCRIPTION OF THE PREFERRED EMBODIMENTS

The salts of sulfonanilide compounds having the formula (I) include alkali metal salts such as sodium and potassium salts; ammonium salts such as ammonium, diethylammonium salts; and acid addition salts such as hydrochloride and sulfuric acid salt.

In the formula (I), the halogen atom includes fluorine, chlorine, bromine and iodine atoms and the alkyl group for $(C_1-C_4)$ alkyl or $(C_1-C_4)$ alkoxy group includes methyl, ethyl, n-propyl, isopropyl, n-butyl, sec-butyl, isobutyl and tert.butyl groups, and especially methyl and ethyl groups and the $(C_2-C_4)$ acyl group includes acetyl, propionyl and butyryl groups and the $(C_3-C_4)$ alkenyl group includes allyl, 1-butenyl, 2-butenyl and 3-butenyl groups.

The sulfonanilide compounds having the formula (I) are classified to the following groups.

A: Compounds (I)
  $X_1$, $X_2$; $R_2$, $R_3$, $R_4$: hydrogen atom; $R_1$: trifluoromethyl group;
  n: 0-2;
  and salts thereof.

B: Compounds (I)
  $X_1$, $X_2$: hydrogen atom or a halogen atom;
  $R_1$: a $(C_1-C_4)$ alkyl group or trifluoromethyl group;
  $R_2$: hydrogen atom, a $(C_1-C_4)$ alkyl group or trifluoromethyl group;
  $R_3$: hydrogen atom or $-SO_2R_1$ group;
  $R_4$: hydrogen atom;
  n: 0 to 2; and $R_1$ is a $(C_1-C_4)$ alkyl group when $X_1$, $X_2$, $R_2$, $R_3$ and $R_4$ are respectively hydrogen atoms, and salts thereof.

It is preferable to use the compounds having the formula (II) among the sulfonanilide compounds having the formula (I) from the viewpoint of herbicidal activity

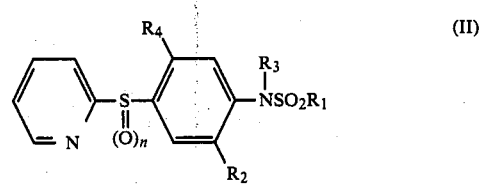

wherein $R_1$ is methyl group or trifluoromethyl group; $R_2$ is hydrogen atom or trifluoromethyl group; $R_3$ is hydrogen atom, methylsulfonyl group or acetyl group; $R_4$ is hydrogen atom or chlorine atom and n is 0 or an integer of 1 to 2; and a salt thereof.

The compounds having the formula (II) are further classified to the following groups a to e. The compounds in the Group a are especially effective.

a: Compounds (II)
  $R_1$: methyl group; $R_2$: trifluoromethyl group; p2 $R_3$, $R_4$: hydrogen atom; n: 0 to 2;
b: Compounds (II)
  $R_1$: trifluoromethy group; $R_2$, $R_3$, $R_4$: hydrogen atom;
  n: 0 to 2
c: Compounds (II)
  $R_1$: methyl group; $R_2$: trifluoromethyl group;
  $R_3$: hydrogen atom; $R_4$: chlorine atom; n: 0 to 2
d: Compounds (II)
  $R_1$: methyl group; $R_2$: trifluoromethyl group;
  $R_3$: acetyl group; $R_4$: hydrogen atom; n: 0 to 2.
e: Compounds (II)
  $R_1$: methyl group; $R_2$: trifluoromethyl group;

$R_3$: methylsulfonyl group; $R_4$: hydrogen atom; n: 0 to 2.

The sulfonanilide compounds having the formula (I) can be produced by the following methods and the method (I) is especially advantageous.

Method (I):

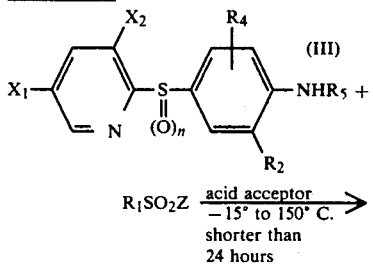
(III)

$R_1SO_2Z$ $\xrightarrow[\text{shorter than 24 hours}]{\text{acid acceptor} \atop -15° \text{ to } 150° \text{ C.}}$ (IV)

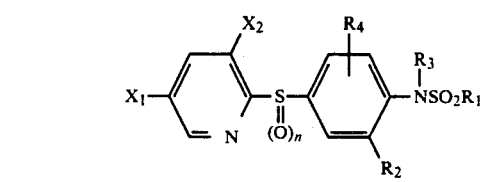
(I)

wherein $X_1$, $X_2$, $R_1$, $R_2$, $R_3$, $R_4$ and n are defined above; Z is a halogen atom or $-OSO_2R_1$ group; and $R_5$ is hydrogen atom, a ($C_2$-$C_4$) acyl group, a ($C_2$-$C_4$) acylmethyl group, a ($C_1$-$C_4$) alkyl group, a ($C_1$-$C_4$) alkoxy ($C_1$-$C_4$) alkyl group or a ($C_3$-$C_4$) alkenyl group.

In the reaction, the acid acceptor can be organic bases such as dimethylaniline, triethylamine, and pyridine; and inorganic bases such as potassium carbonate, sodium carbonate, potassium hydroxide and sodium hydroxide.

The solvent can be glyme, benzene, methylene chloride and chloroform.

The sulfonic acid derivatives having the formula (IV) used as the starting material are disclosed in U.S. Pat. No. 4,005,141.

The aniline compounds having the formula (III) can be produced by the following conventional methods. (1) The process for producing the aniline compound by reacting a 2-halopyridine with a 4-aminothiophenol at 50° to 100° C. for 1 to 5 hours (2) The process for producing the aniline compound by reacting a 2-mercaptopyridine with a 4-nitro-halobenzene to produce a 4-(pyridine-2-ylthio) nitrobenzene and reducing the nitro group in the compound or oxidizing a sulfide to sulfoxide or sulfone and then, reducing the nitro group in the compound.

Method (II):

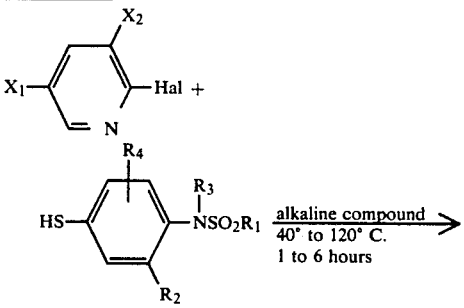

(V)

(VI)

-continued

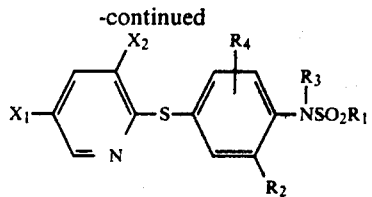
(VII)

wherein $X_1$, $X_2$, $R_1$, $R_2$, $R_3$, and $R_4$ are defined above and Hal is a halogen atom.

In the reaction, the alkaline compound can be inorganic bases such as sodium hydroxide, potassium hydroxide, sodium carbonate, and potassium carbonate.

The solvent can be aprotic polar solvents such as dimethylformamide, dimethylacetamide, sulfolane and dioxane.

The pyridine compounds having the formula (V) are disclosed in U.S. Pat. No. 4,046,553.

The thiophenols having the formula (VI) can be easily produced by reacting 4-aminothiophenol with the sulfonic acid derivative as the same with method (I).

Method (III):

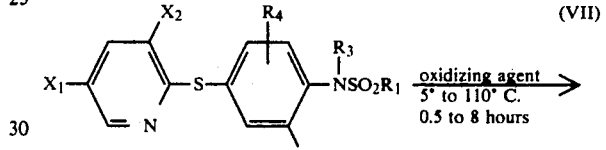
(VII) $\xrightarrow[\text{0.5 to 8 hours}]{\text{oxidizing agent} \atop 5° \text{ to } 110° \text{ C.}}$

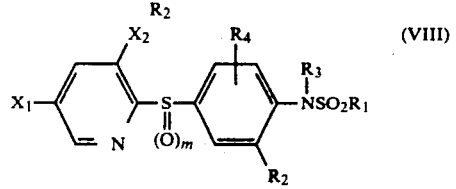
(VIII)

wherein $X_1$, $X_2$, $R_1$, $R_2$, $R_3$, and $R_4$ are defined above and m is 1 or 2.

In the reaction, the oxidizing agent can be hydrogen peroxide, peracetic acid and perbenzoic acid.

Method (IV):

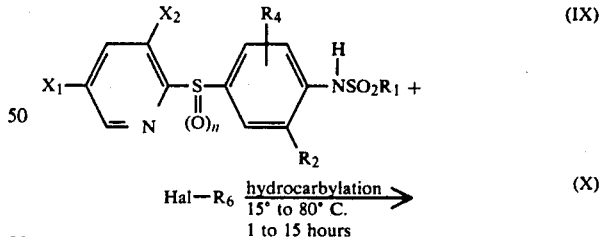
(IX)

Hal—$R_6$ $\xrightarrow[\text{1 to 15 hours}]{\text{hydrocarbylation} \atop 15° \text{ to } 80° \text{ C.}}$ (X)

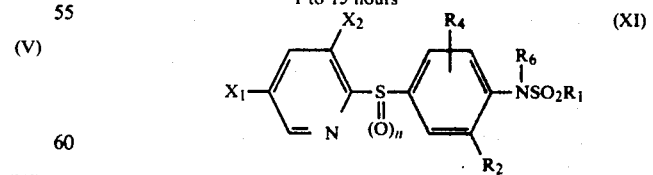
(XI)

wherein $X_1$, $X_2$, $R_1$, $R_2$, $R_4$, n and Hal are defined above, and $R_6$ is a ($C_2$-$C_4$) acylmethyl group, a ($C_1$-$C_4$) alkyl group, a ($C_1$-$C_4$) alkoxy ($C_1$-$C_4$) alkyl group or a ($C_3$-$C_4$) alkenyl group.

In the reaction, it is possible to use an alkaline compound such as sodium hydroxide, potassium hydroxide, sodium carbonate and potassium carbonate; and an aprotic polar solvent such as dimethylformamide, dimethylacetamide, sulfolane and dioxane.

The resulting sulfonanilide compounds can be converted to salts thereof by the following methods. (1) When $R_3$ is hydrogen atom in the formula (I), the sulfonanilide compound is reacted with an alkaline material such as alkali metal or alkaline earth metal oxide, hydroxide or carbonate; ammonia; and organic amines, by the conventional method. (2) The sulfonanilide compound having the formula (I) is reacted with an inorganic acid such as hydrochloric acid and sulfuric acid by the conventional method.

Certain preparation examples for producing the compounds of the present invention will be illustrated.

Preparation Example 1

4-(Pyridine-2-ylthio) trifluoromethanesulfonanilide

A mixture of 22.7 g of 2-chloropyridine, 25 g of 4-aminothiophenol, 12.4 g of potassium hydroxide and 100 ml of dioxane was heated at 60° C. for about 2 hours to react them, and the product was purified to obtain 34.2 g of 4-(pyridine-2-ylthio) aniline. A mixture of 10 g of 4-(pyridine-2-ylthio) aniline, 5.6 g of triethylamine and 70 ml of chloroform was cooled at lower 5° C. in nitrogen gas atmosphere and 17 g of trifluoromethanesulfonic anhydride was added dropwise to the mixture. After the addition, the mixture was further stirred at 40° to 50° C. for about 1 hour to react them.

The reaction mixture was treated with 100 ml of 10% HCl and then, chloroform was distilled off under a reduced pressure and a residue was dissolved in 150 ml of 10% aqueous solution of sodium hydroxide.

The solution was extracted with ether and the aqueous phase was acidified with 10% HCl to obtain oily product.

The oily product was extracted with ether and dried with anhydrous sodium sulfate and then ether was distilled off and the product was recrystallized from a mixture of cyclohexane and ethanol to obtain 2.5 g of the object compound having a melting point of 155° to 157° C.

The object compound was treated with sodium hydroxide by the conventional method to obtain sodium salt of 4-(pyridine-2-ylthio) trifluoromethanesulfonanilide (m.p. 310° C.).

Preparation Example 2

4-(Pyridine-2-ylsulfonyl)trifluoromethanesulfonanilide

In 70 ml of acetic acid, 3.3 g of 4-(pyridine-2-ylthio) trifluoromethanesulfonanilide obtained by the Preparation Example 1 was dissolved and heated at 60° to 70° C. and then, 3.4 g of 30% $H_2O_2$ aq. solution was added dropwise to the solution and the reaction was continued at the same temperature for about 2 hours.

The reaction mixture was poured into 200 ml of water and the oily product was extracted with ether and washed with an aqueous solution of sodium bicarbonate and then, with water and then, dried with anhydrous sodium sulfate and ether was distilled off and the product was recrystallized from ethanol to obtain 2.8 g of the object product having a melting point of 173° to 175° C.

The process was followed except varying hydrogenperoxide, 4-(pyridine-2-ylsulfinyl) trifluoromethanesulfonanilide (m.p. 160° to 163° C.) was obtained.

Preparation Example 3

N-methylsulfonyl-2-trifluoromethyl-4-(pyridine-2-ylthio) methanesulfonanilide (1) Synthesis of 2-trifluoromethyl-4-(pyridine-2-ylthio) aniline A mixture of 25 g of 2-mercaptopyridine, 70 ml of dimethylacetamide and 45.7 g of 3-trifluoromethyl-4-nitrochlorobenzene was heated at 80° to 90° C. and 35 g of 40% NaOH aq. solution was added to the mixture. After the reaction, the reaction mixture was poured into water and the product was extracted with ethyl ether and the ether phase was washed with a dilute NaOH aq. solution and then, with water and dried with anhydrous sodium sulfate and ether was distilled off to obtain 52 g of 2-trifluoromethyl-4-(pyridine-2-ylthio) nitrobenzene.

A mixture of 30 g of the obtained nitrobenzene, 100 ml of ethanol and 75 ml of hydrochloric acid was stirred at lower than 80° C. and 80 g of stannous chloride was added to the mixture and the reaction was carried out under a refluxing condition for 2 hours.

After the reaction, ethanol and hydrochloric acid were distilled off and 40% NaOH aq. solution was added and the product was extracted with ethyl and dried and then, ether was distilled off and the product was recrystallized from a mixture of cyclohexane and ethanol to obtain 18 g of 2-trifluoromethyl-4-(pyridine-2-ylthio) aniline (m.p. 132° to 133° C.).

(2) Preparation of Object Compound

A mixture of 13.5 g of 2-trifluoromethyl-4-(pyridine-2-ylthio) aniline obtained in the previous step and 33.1 g of pyridine was stirred at 0° to 5° C. and 14.3 g of methanesulfonyl chloride was added to the mixture during 2 hours. The mixture was stirred at room temperature for 15 hours to react them. After the reaction, the reaction mixture was poured into a mixture of 80 ml of ice water and 20 ml of conc. hydrochloric acid and the solid product was recrystallized from a mixture of benzene and ethanol to obtain 15 g of the object compound (m.p. 145° to 146° C.).

Preparation Example 4

2-Trifluoromethyl-4-(pyridine-2-ylthio)methanesulfonanilide

A mixture of 6 g of N-methylsulfonyl-2-trifluoromethyl-4-(pyridine-2-ylthio) methanesulfonanilide obtained in the Preparation Example 3, 2.8 g of 85% KOH and 30 ml of methanol was stirred at room temperature for 10 hours to react them. Methanol was distilled off and the solid residue was dissolved in a hot water and the solution was filtered. The filtrate was acidified with a dilute hydrochloric acid and the precipitate was separated and recrystallized from a mixed solvent of benzene and ethanol to obtain 3.5 g of the object compound (m.p. 130° to 134° C.).

Preparation Example 5

2-Trifluoromethyl-4-(pyridine-2-ylsulfinyl) methanesulfonanilide

A mixture of 70 ml of glacial acid and 3.5 g of 2-trifluoromethyl-4-(pyridine-2-ylthio) methanesulfonanilide was stirred at 10° C. and 1.13 g of 30% $H_2O_2$ was added and the mixture was stirred for 5 hours to react them and it was kept at room temperature for 15 hours. The reaction mixture was poured into 300 ml of water and the resulting precipitate was recrystallized from a mixed solvent of benzene and ethanol to obtain 2.5 g of the object compound (m.p. 126° to 128° C.).

Preparation Example 6

2-Trifluoromethyl-4-(pyridine-2-ylsulfonyl) methanesulfonanilide

A mixture of 70 ml of glacial acetic acid and 3.5 g of 2-trifluoromethyl-4-(pyridine-2-ylthio) methanesulfonanilide was stirred at 60° C. and 3.4 g of 30% $H_2O_2$ was added and the mixture was further stirred for 2 hours to react them. After the reaction, the reaction mixture was poured into 300 ml of water and the resulting precipitate was separated and recrystallized from a mixture of benzene and ethanol to obtain 2.7 g of the object compound (m.p. 141° to 143° C.).

Preparation Example 7

Sodium salt of 2-trifluoromethyl-4-(pyridine-2-ylsulfonyl) methanesulfonanilide

In 50 ml of acetone, 1.2 g of 2-trifluoromethyl-4-(pyridine-2-ylsulfonyl) methanesulfonanilide was dissolved and 0.32 g of anhydrous sodium carbonate was added to the solution and the mixture was stirred at room temperature for 15 hours to react them. The reaction mixture was filtered and concentrated to dry it and the resulting while solid product was recrystallized from isopropanol to obtain 0.9 g of the object product (m.p. 199° to 204° C.).

Preparation Example 8

4-(5-Chloropyridine-2-ylthio)trifluoromethanesulfonanilide

A mixture of 29.6 g of 2,5-dichloropyridine, 25 g of 4-aminothiophenol, 12.4 g of KOH and 100 ml of dimethyl acetamide was stirred at 80° C. for about 3 hours to react them.

The reaction product was purified to obtain 35.4 g of 4-(5-chloropyridine-2-ylthio) aniline.

A mixture of 11.8 g of 4-(5-chloropyridine-2-ylthio) aniline, 5.5 g of triethylamine and 80 ml of chloroform was stirred at lower than 5° C. and 15.2 g of trifluoromethanesulfonic anhydride was added dropwise and the mixture was further stirred at room temperature for 2 hours after the addition to react them. The reaction mixture was treated with 10% HCl aq. solution and chloroform phase was treated with 10% NaOH aq. solution to extract the product and the alkaline water phase was acidified to form an oily product. The oily product was extracted with ethyl ether and dried with anhydrous sodium sulfate and ether was distilled off and the product was recrystallized from a mixture of benzene and cyclohexane to obtain 5.6 g of the object compound (m.p. 166° to 168° C.).

Preparation Example 9

2-Methyl-4-(pyridine-2-ylthio)trifluoromethanesulfonanilide

A mixture of 15 ml of dimethylacetamide, 2.2 g of 2-chloropyridine, 5.2 g of 2-methyl-4-mercaptotrifluoromethanesulfonanilide and 1.9 g of 40% NaOH aq. solution was stirred at 70° to 80° C. for 2 hours to react them. The reaction mixture was poured into water to precipitate crystals and the crystals were filtered and recrystallized from a mixture of toluene and n-hexane to obtain 3 g of the object compound (m.p. 83° to 85° C.).

Preparation Example 10

N-acetyl-2-trifluoromethyl-4-(pyridine-2-ylthio)methanesulfonanilide

In methylene chloride, 5.0 g of 2-trifluoromethyl-4-(pyridine-2-ylthio) aniline was dissolved and 2.5 g of pyridine was added and the mixture was cooled with ice and 2.1 g of acetylchloride was added. The mixture was refluxed for about 1 hour to react them. The reaction mixture was poured into water and methylene chloride layer was washed with water and dried with anhydrous sodium sulfate and then, methylene chloride was distilled off under a reduced pressure to obtain 4.8 g of 2-trifluoromethyl-4-(pyridine-2-ylthio) acetanilide (m.p. 119° to 120° C.).

A mixture of 3.0 g of 2-trifluoromethyl-4-(pyridine-2-ylthio) acetanilide, 20 ml of dimethylacetamide and 1.2 g of sodium hydride was stirred at 0° C. and 5.5 g of methanesulfonylchloride was added to it and the mixture was stirred at 0° C. for one night to react them. The reaction mixture was poured into water and the product was extracted with methylene chloride and the solution was washed with $Na_2CO_3$aq. solution and then, with water and dried with anhydrous sodium sulfate and methylene chloride was distilled off to obtain 2.0 g of the object compound.

Preparation Example 11

N-{2-(ethoxy)ethyl}-2-trifluoromethyl-4-(pyridine-2-ylthio)methanesulfonanilide

To 5 ml of dimethylacetamide were added 3.0 g of 2-trifluoromethyl-4-(pyridine-2-ylthio)methanesulfonanilide, 1.3 g of 2-(ethoxy)ethylbromide and 0.5 g of potassium hydroxide, and the mixture was stirred at 60° C. for 4 hours to react them. After the reaction, 50 ml of methylene chloride was added to the reaction mixture and the solution was poured into water and washed with KOH aq. solution and then, with water and dried with anhydrous sodium sulfate and methylene chloride was distilled off to obtain 2.5 g of the object compound.

Preparation Example 12

2-Trifluoromethyl-4-(pyridine-2-ylthio) methanesulfonanilide hydrochloride

In 100 ml of ethyl ether, 3 g of 2-trifluoromethyl-4-(pyridine-2-ylthio) methanesulfonanilide was dissolved and hydrogen-chloride gas dried with sulfuric acid and calcium chloride was injected into the resulting solution to precipitate a solid product and the solid product was filtered to obtain 2.8 g of the object compound.

Typical examples of the sulfonanilide compounds of the formula (I) of the present invention are given below:

Table 1

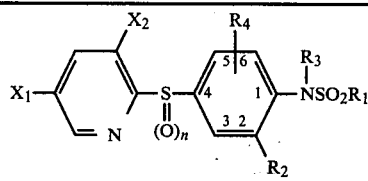

| Compound | X₁ | X₂ | n | R₁ | R₂ | R₃ | R₄ | Physical constant |
|---|---|---|---|---|---|---|---|---|
| 1 | H | H | 0 | $CF_3$ | H | H | H | m.p.155°–157° C. |
| 2 | H | H | 1 | $CF_3$ | H | H | H | m.p.160°–163° C. |
| 3 | H | H | 2 | $CF_3$ | H | H | H | m.p.173°–175° C. |
| 4 | H | H | 0 | $CF_3$ | H | Na | H | m.p.310° C. |
| 5 | Cl | H | 0 | $CH_3$ | H | H | H | m.p.185°–188° C. |
| 6 | Br | H | 0 | $CH_3$ | H | H | H | m.p.192°–195° C. |
| 7 | Cl | H | 2 | $CH_3$ | H | H | H | m.p.180°–188° C. |
| 8 | Cl | Cl | 0 | $CH_3$ | H | H | H | m.p.205°–210° C. |
| 9 | Cl | Cl | 2 | $CH_3$ | H | H | H | m.p.235°–240° C. |
| 10 | H | H | 0 | $CH_3$ | $CF_3$ | H | H | m.p.130°–134° C. |
| 11 | H | H | 1 | $CH_3$ | $CF_3$ | H | H | m.p.126°–128° C. |
| 12 | H | H | 2 | $CH_3$ | $CF_3$ | H | H | m.p.141°–143° C. |
| 13 | H | H | 0 | $CH_3$ | $CH_3$ | H | H | m.p.140°–142° C. |
| 14 | H | H | 2 | $CH_3$ | $CH_3$ | H | H | |
| 15 | H | H | 0 | $CH_3$ | $CH_3$ | $-SO_2CH_3$ | H | m.p.123°–125° C. |
| 16 | Cl | H | 1 | $CH_3$ | H | H | H | m.p.180°–186° C. |
| 17 | H | H | 0 | $CH_3$ | H | $-SO_2CH_3$ | H | m.p.202°–206° C. |
| 18 | H | H | 0 | $CH_3$ | H | H | H | m.p.130°–132° C. |
| 19 | H | H | 2 | $CH_3$ | H | H | H | |
| 20 | H | H | 0 | $CH_3$ | $CF_3$ | $-SO_2CH_3$ | H | m.p.145°–146° C. |
| 21 | H | H | 2 | $CH_3$ | $CF_3$ | Na | H | m.p.199°–204° C. |
| 22 | Cl | H | 0 | $CF_3$ | H | H | H | m.p.166°–168° C. |
| 23 | Cl | H | 1 | $CF_3$ | H | H | H | m.p.170°–174° C. |
| 24 | Cl | H | 2 | $CF_3$ | H | H | H | m.p.234°–237° C. |
| 25 | H | H | 0 | $CF_3$ | $CH_3$ | H | H | m.p.83°–85° C. |
| 26 | H | H | 2 | $CF_3$ | $CH_3$ | H | H | |
| 27 | Br | H | 2 | $CH_3$ | H | H | H | m.p.230°–235° C. |
| 28 | H | H | 0 | $CH_3$ | $NO_2$ | H | H | m.p.134°–138° C. |
| 29 | H | H | 0 | $CH_3$ | $CF_3$ | H | 5-Cl | m.p.130°–133° C. |
| 30 | H | H | 2 | $CH_3$ | $CF_3$ | H | 5-Cl | m.p.174°–177° C. |
| 31 | Br | H | 0 | $CH_3$ | $CF_3$ | H | H | |
| 32 | Br | H | 2 | $CH_3$ | $CF_3$ | H | H | m.p.211°–215° C. |
| 33 | Cl | Cl | 0 | $CH_3$ | $CF_3$ | H | H | m.p.95°–100° C. |
| 34 | Cl | Cl | 1 | $CH_3$ | $CF_3$ | H | H | m.p.140°–144° C. |
| 35 | Cl | Cl | 2 | $CH_3$ | $CF_3$ | H | H | m.p.150°–153° C. |
| 36 | $CH_3$ | H | 2 | $CH_3$ | $CF_3$ | H | H | m.p.172°–176° C. |
| 37 | H | H | 1 | $CH_3$ | $CF_3$ | $-SO_2CH_3$ | H | m.p.64°–68° C. |
| 38 | H | H | 2 | $CH_3$ | $CF_3$ | $-SO_2CH_3$ | H | m.p.71°–75° C. |
| 39 | H | H | 2 | $CH_3$ | $CF_3$ | $-C_2H_5$ | H | |
| 40 | H | H | 0 | $CH_3$ | $CF_3$ | $-COCH_3$ | H | |
| 41 | $CH_3$ | H | 2 | $CH_3$ | $CF_3$ | $-SO_2CH_3$ | H | m.p.143°–145° C. |
| 42 | Cl | Cl | 0 | $CH_3$ | $CF_3$ | $-SO_2CH_3$ | H | m.p.182°–184° C. |
| 43 | H | H | 0 | $CH_3$ | $CF_3$ | $-CH_2CH=CH_2$ | H | m.p.92°–94° C. |
| 44 | H | H | 2 | $CH_3$ | $CF_3$ | $-CH_2CH=CH_2$ | H | |
| 45 | H | H | 0 | $CH_3$ | $CF_3$ | $-COC_2H_5$ | H | |
| 46 | H | H | 2 | $CH_3$ | $CF_3$ | $-COC_2H_5$ | H | |
| 47 | H | H | 0 | $CH_3$ | $CF_3$ | H | H | |
| 48 | H | H | 0 | $CH_3$ | $CF_3$ | $-C_2H_5$ | H | |
| 49 | H | H | 0 | $CH_3$ | $CF_3$ | $-C_2H_4OC_2H_5$ | H | |
| 50 | $CH_3$ | H | 0 | $CH_3$ | $CF_3$ | H | H | |
| 51 | H | H | 0 | $C_2H_5$ | $CF_3$ | H | H | |
| 52 | H | H | 2 | $C_2H_5$ | $CF_3$ | H | H | |
| 53 | H | H | 0 | $CH_2Cl$ | $CF_3$ | H | H | m.p.110°–112° C. |
| 54 | H | H | 2 | $CH_2Cl$ | $CF_3$ | H | H | m.p.238°–241° C. |
| *55 | H | H | 0 | $CH_3$ | $CF_3$ | H | H | m.p.140°–146° C. |
| 56 | H | H | 0 | $CH_3$ | $CF_3$ | $-CH_2COCH_3$ | H | |
| 57 | H | H | 2 | $CH_3$ | $CF_3$ | $-CH_2COCH_3$ | H | m.p.203°–207° C. |

*HC salt

The sulfonanilide compounds of the present invention have excellent herbicidal effects as the active ingredients of agricultural compositions as shown in the following Test Examples.

The herbicidal characteristics are as follows.

(1) The sulfonanilide compounds of the present invention impart excellent herbicidal effect to annual gramineous weeds such as barnyard grass, large crabgrass, water foxtail; perennial gramineous weeds such as Johnsongrass (*Sorghum halepense* Pers), bermudagrass (*Cynodon dactylon* Pers) and quackgrass (*Agropyron repens* Beauv) and also annual broad-leafed weeds such as wavy bittercress, blue lettuce, lamb's-quarters (*Chenopodium album* L.) and redroot pigweed (*Amaranthus retroflexus* L.). The sulfonanilide compounds are especially effective to control the growth of subterranean part (root) and aerial part (shoot) of perennial gramineous weeds and to prevent the regrowth thereof.

(2) The sulfonanilide compounds of the present invention impart preferable herbicidal effect to cyperaceae weeds and especially control not only the growth of aerial part of nutsedge which is one of highly noxious weeds, by pre-plant soil incorporation, pre-emergence soil treatment or foliar treatment, but also the growth of subterranean stem including rhizone and tuber and further prevent the regrowth thereof.

(3) The sulfonanilide compounds of the present invention are not substantially phytotoxic to broad-leafed crops such as cotton and peanuts. Accordingly, it is possible to control selectively the highly noxious weeds in upland farms for crop plant.

The herbicides of the sulfonanilide compounds of the present invention can be applied in various places such as upland farms, paddy fields, orchards, mulberry farms, forests, ridges, grounds, factory sites. They may be applied by soil surface treatments, soil incorporation, foliar treatments, etc. The herbicidal compounds can be applied in the form of an aqueous dispersion, an emulsifiable concentrate, water-miscible solution, a wettable powder, a dust or a granule with adjuvants such as diluent, a solvent, an emulsifier and a wetting agent.

The adjuvants include solid carriers such as diatomaceous earth, slaked lime, calcium carbonate, talc, fine silicon dioxide, kaolin, bentonite, jeeklite, vermiculite and sand; solvents such as benzene, toluene, xylene, solvent naphtha, ethanol, dioxane, isophorone, methyl ethyl ketone, methyl isobutyl ketone, dimethylformamide, dimethylsulfoxide, N-methylpyrrolidone and water and optionally anionic or nonionic surfactants such as sodium alkylsulfate, sodium alkylbenzenesulfonate, sodium lignin sulfonate, polyoxyethylene lauryl ether, polyoxyethylene alkylaryl ether, polyoxyethylene fatty acid ester, polyoxyethylene sorbitan fatty acid ester, sodium naphtalenesulfonateformaldehyde condensate, sulfate of polyoxyethylene alkylaryl ether, polyethyleneglycol oleyl ether, and polyethyleneglycol dodecylphenyl ether, and further optionally bilders such as sodium carbonate, potassium carbonate, sodium tripolyphosphate, sodium metasilicate, and binders such as polyvinyl alcohol, carboxymethylcellulose, arabic gum, starch, casein.

The ratios of the components in the composition are dependent upon the forms of the compositions.

|  | Usual ratio (wt. %) | Preferable ratio (wt. %) |
|---|---|---|
| Active ingredient | 1 to 90 | 1 to 70 |
| Carrier or solvent | 5 to 99 | 25 to 99 |
| Surfactant | 0 to 30 | 1 to 20 |

Further, the ratios of the components in the each composition are illustrated below.

| Granule: | |
|---|---|
| Active ingredient | 1 to 30 wt. % |
| Carrier | 60 to 99 wt. % |
| Surfactant | 0 to 15 wt. % |
| Wettable powder: | |
| Active ingredient | 20 to 85 wt. % |
| Carrier | 5 to 75 wt. % |
| Surfactant | 5 to 10 wt. % |
| Dust: | |
| Active ingredient | 3 to 20 wt. % |
| Carrier | 75 to 97 wt. % |
| Surfactant | 0 to 5 wt. % |
| Emulsifiable concentrate: | |
| Active ingredient | 10 to 50 wt. % |
| Solvent | 25 to 80 wt. % |
| Surfactant | 10 to 30 wt. % |

The sulfonanilide compounds of the present invention can be used with the other agricultural chemicals such as the other herbicides, insecticides and fungicides; and fertilizers and soils. Synergism may be imparted in certain combinations.

The doses of the sulfonanilide compounds of the present invention vary depending upon such conditions as the weather, the soil, the form of the composition, the season, the method of application and the type of weeds treated. The dose of the active ingredient is usually in a range of 0.1 to 1,000 g per are, preferably 2.5 to 500 g per are, and more preferably 5 to 100 g per are (are = 100 m$^2$).

Although certain preparations of the compounds, herbicidal experiments of the compounds and compositions of the compounds are described as the examples, it will be apparent to one of ordinary skill in the art that many changes and modifications can be made thereto without departing from the scope of the invention as set forth herein.

Test Example 1

Each 1/1,000 are (1/10 m$^2$) pot was filled with soil containing seeds of weeds and a specific amount of each active ingredient was mixed by soil incorporation to form the treated layer having a depth of about 5 cm and then, seeds of soybean, cotton, flax, rape, cucumber, maize, wheat and rice were sown in the treated layer and also tuber of purple nutsedge was planted.

In a green house, they were grown under the conventional growth management. Twenty five days after the seed sown, the growth condition of each of the plants and weeds was observed. The degree of growth control is shown in Table 2 by the following standards rating 10 degrees.

10: Complete growth control without no germination
1: Growth condition same with that of untreated plant or weed without no growth control.

Table 2

|  | Active ingredient | | | |
|---|---|---|---|---|
|  | Compound No. 1 | | Compound No. 3 | |
| Amount of active ingredient (g/are) | 10 | 20 | 10 | 20 |
| Crop Plants | | | | |
| Soybean | 1 | 1 | 3 | 3 |
| Cotton | 1 | 1 | 1 | 3 |
| Flax | 1 | 1 | 3 | 3 |
| Rape | 2 | 3 | 6 | 9 |
| Cucumber | 5 | 5 | 10 | 10 |
| Maize | 8 | 10 | 9 | 10 |
| Wheat | 10 | 10 | 10 | 10 |
| Rice | 10 | 10 | 10 | 10 |
| Weeds | | | | |
| Purple nutsedge | 6 | 10 | 8 | 10 |
| Large crabgrass | 10 | 10 | 10 | 10 |
| Water foxtail | 10 | 10 | 10 | 10 |
| Wavy bittercress | 7 | 10 | 10 | 10 |
| Blue lettuce | 10 | 10 | 10 | 10 |

Purple nutsedge (*Cyperus rotundus* L)
Large crabgrass (*Digitaria adscendens* Henr)
Water foxtail (*Alopecurus aequalis* Sobol. var. *amurensis* Ohwi)
Wavy bittercress (*Cardamine flexuosa* With)
Blue lettuce (*Ixeris dentata* Nakai)

Test Example 2

Each 1/1,000 are (1/10 m²) pot was filled with soil containing seeds of weeds and a specific amount of each active ingredient was mixed by soil incorporation at a ratio of 40 g of each active ingredient per are to form the treated layer having a depth of about 5 cm and then tuber of purple nutsedge was planted.

In a green house, they were grown under the conventional growth management. Thirty days after the soil incorporation, naturally grown weeds were grouped to gramineous weeds such as large crabgrass and barnyard grass (*Echinochloa crus-galli* Beauv) and broad-leafed weeds such as posumbu knotweed (*Polygonum longisetum* De Bruyn), blue lettuce and Philadelphia fleabane (*Erigeron philadelphicus* L.). The growth degree of these weeds and purple nutsedge were observed. The results of Degree of growth control under the standard of Test Example 1 are shown in Table 3.

Table 3

| Active ingredient | Degree of Growth Control | | |
|---|---|---|---|
| | Gramineous weeds | Broad leafed weeds | Purple nutsedge |
| Compound No. 5 | 7 | 7 | 7 |
| No. 7 | 7 | 6 | 3 |
| No. 8 | 4 | — | 4 |
| No. 9 | 3 | — | 4 |
| No. 10 | 9 | 6 | 10 |
| No. 11 | 10 | 9 | 10 |
| No. 12 | 10 | 10 | 10 |
| No. 17 | 3 | — | — |
| No. 20 | 5 | 3 | 9 |
| No. 22 | 10 | 10 | 9 |
| No. 23 | 10 | 7 | 9 |
| No. 24 | 10 | 10 | 7 |
| No. 30 | 10 | 9 | 10 |
| No. 37 | 10 | 10 | 10 |
| No. 38 | 10 | 10 | 10 |
| No. 40 | 10 | 10 | 10 |

Test Example 3

In accordance with the method of the Test Example 2 except sowing seeds of cotton and peanut at the time planting tuber of purple nutsedge and decreasing the amount of each active ingredient, the test was carried out. The results are shown in Table 4.

Table 4

| Active ingredient | Amount of active ingredient (g/are) | Degree of Growth Control | | | | |
|---|---|---|---|---|---|---|
| | | Cotton | Peanut | Gram. weeds | Broad leafed weeds | Purple nutsedge |
| Compound No. 10 | 10 | 1 | 1 | 8 | — | 9 |
| | 20 | 1 | 1 | 10 | 4 | 10 |
| No. 11 | 10 | 1 | 1 | 8 | 8 | 9 |
| | 20 | 1 | 1 | 10 | 8 | 10 |
| No. 12 | 10 | 1 | 1 | 10 | 9 | 10 |
| | 20 | 1 | 1 | 10 | 10 | 10 |
| No. 22 | 10 | 1 | 1 | 9 | 8 | 6 |
| | 20 | 1 | 1 | 10 | 10 | 9 |
| No. 23 | 10 | 1 | 1 | 6 | 4 | 6 |
| | 20 | 1 | 1 | 10 | 6 | 7 |
| No. 24 | 10 | 1 | 1 | 8 | 4 | 4 |
| | 20 | 1 | 1 | 10 | 9 | 6 |
| No. 38 | 10 | 1 | 1 | 10 | 8 | 9 |
| | 20 | 1 | 1 | 10 | 10 | 10 |
| No. 40 | 10 | 1 | 1 | 9 | 8 | 9 |
| | 20 | 1 | 1 | 10 | 10 | 10 |

Test Example 4

Each 1/1,000 are (1/10 m²) pot was filled with soil containing seeds of weeds and tuber of purple nutsedge was planted and covered with soil. Each aqueous dispersion of specific amount of each active ingredient was sprayed on the surface of the soil. Eighty days after the treatment, the degree of growth control of weeds was observed under the standard of the Test Example 1. The results are shown in Table 5.

Table 5

| Active ingredient | Amount of active ingredient (g/are) | Degree of Growth Control | | |
|---|---|---|---|---|
| | | Gramineous weeds | Broad leafed Weeds | Purple nutsedge |
| Compound No. 10 | 10 | 9 | — | 7 |
| | 20 | 10 | 5 | 9 |
| | 40 | 10 | 10 | 9 |
| No. 11 | 10 | 9 | 4 | 7 |
| | 20 | 10 | 6 | 9 |
| | 40 | 10 | 9 | 9 |
| No. 12 | 10 | 9 | 9 | 7 |
| | 20 | 10 | 10 | 9 |
| | 40 | 10 | 10 | 9 |
| No. 22 | 10 | 8 | 9 | 7 |
| | 20 | 10 | 9 | 8 |
| | 40 | 10 | 9 | 8 |
| No. 23 | 10 | 8 | 7 | — |
| | 20 | 9 | 10 | 5 |
| | 40 | 10 | 9 | 7 |
| No. 24 | 10 | 7 | 5 | 3 |
| | 20 | 8 | 8 | 5 |
| | 40 | 9 | 10 | 7 |
| No. 40 | 10 | 9 | 4 | 7 |
| | 20 | 10 | 6 | 9 |
| | 40 | 10 | 10 | 9 |

Test Example 5

Each 1/5,000 are (1/50 m²) pot was filled with soil and a specific amount of each active ingredient was mixed by soil incorporation to form the treated layer having a depth of about 5 cm. Under the soil surface at a depth of about 2 cm, rhizome of Johnsongrass and stolon of bermudagrass were respectively planted at two parts and rhizome of quack grass was planted at one part and they were grown. Eighty days after the treatment, the degree of growth control was observed, under the standard of Text Example 1. The results are shown in Table 6.

Table 6

| Active ingredient | Amount of active ingredient (g/are) | Degree of Growth Control | | |
|---|---|---|---|---|
| | | Johnsongrass | Bermudagrass | Quackgrass |
| Compound No. 10 | 10 | 4 | 10 | 9 |
| | 20 | 6 | 10 | 10 |
| | 40 | 9 | 10 | 10 |
| No. 11 | 10 | 9 | 10 | 10 |
| | 20 | 10 | 10 | 10 |
| | 40 | 10 | 10 | 10 |
| No. 37 | 10 | 9 | 8 | 9 |
| | 20 | 10 | 10 | 10 |
| | 40 | 10 | 10 | 10 |
| No. 38 | 10 | 9 | 9 | 10 |
| | 20 | 10 | 10 | 10 |
| | 40 | 10 | 10 | 10 |
| 2-methyl-4-(phenylsulfonyl) trifluoromethane-sulfonanilide (USP 4,005,141) | 10 | 1 | 1 | 2 |
| | 40 | 2 | 5 | 4 |

Test Example 6

Each 1/5,000 are (1/50 m²) pot was filled with soil. Under the soil surface at a depth of about 2 cm, stolon of bermudagrass and tuber of purple nutsedge were planted and they were grown.

When purple nutsedge was grown to 6 to 8 leaves stage, each aqueous dispersion of each active ingredient with 0.5% of a wetting agent was sprayed on the leaves and stems at a rate of 5 liter per are. Eighty days after the spray treatment, the degree of growth control was observed under the standard of Test Example 1. The results are shown in Table 7.

Table 7

| Active ingredient | Amount of active ingredient (g/are) | Degree of Growth Control Bermudagrass | Purple nutsedge |
|---|---|---|---|
| Compound | 10 | 9 | 7 |
| No. 10 | 20 | 9 | 8 |
|  | 40 | 10 | 9 |
|  | 10 | 9 | 8 |
| No. 12 | 20 | 9 | 9 |
|  | 40 | 10 | 9 |
| 2-methyl-4-(phenyl-sulfonyl)trifluoro-methanesulfonanilide (USP 4,005,141) | 10 | 1 | 1 |
|  | 20 | 1 | 3 |
|  | 40 | 2 | 4 |

Formulation Example 1

| | |
|---|---|
| 4-(Pyridine-2-ylsulfonyl)trifluoromethane-sulfonanilide | 20 wt. parts |
| Xylene | 60 wt. parts |
| Mixture of a polyoxyethylene phenyl phenol derivative, a polyoxyethylene alkylaryl ether, a polyoxyethylene sorbitan alkylate and an alkylaryl sulfonate | 20 wt. parts |

The components were mixed to obtain an emulsifiable concentrate.

Formulation Example 2

| | |
|---|---|
| N-acetyl-2-trifluoromethyl-4-(pyridine-2-ylthio)methanesulfonanilide | 15 wt. parts |
| Xylene | 65 wt. parts |
| Polyoxyethylene stearate | 20 wt. parts |

The components were mixed to obtain an emulsifiable concentrate.

Formulation Example 3

| | |
|---|---|
| 4-(Pyridine-2-ylsulfonyl)trifluoromethane-sulfonanilide | 3 wt. parts |
| Kaolin powder | 50 wt. parts |
| Talc | 46 wt. parts |
| Sodium naphthalenesulfonate-formaldehyde condensate | 1 wt. part |

The components were uniformly mixed and pulverized to obtain a dust.

The preparation was repeated by using 2-trifluoromethyl-4-(pyridine-2-ylsulfonyl)methanesulfonanilide as the active ingredient to obtain a dust.

Formulation Example 4

| | |
|---|---|
| 4-(Pyridine-2-ylthio)trifluoromethane-sulfonanilide | 40 wt. parts |
| Jeeklite (principal component:kaolinite) | 55 wt. arts |
| Sodium alkylbenzene sulfonate | 2 wt. parts |
| Mixture of equal amounts of fine silicon dioxide and a polyoxyethylene alkylaryl ether | 3 wt. parts |

The components were mixed and pulverized to obtain a wettable powder.

The preparation was repeated by using 2-trifluoromethyl-4-(pyridine-2-ylthio)methanesulfonanilide as the active ingredient to obtain a wettable powder.

Formulation Example 5

| | |
|---|---|
| 4-(Pyridine-2-ylsulfonyl)trifluoromethane-sulfonanilide | 7 wt. parts |
| Bentonite | 58 wt. parts |
| Jeeklite | 30 wt. parts |
| Sodium lignin sulfonate | 5 wt. parts |

The components were mixed and suitable amount of water was added, and the mixture was granulated to obtain granules.

The preparation was repeated by using 4-(5-chloropyridine-2-ylsulfonyl)trifluoromethanesulfonanilide as the active ingredient to obtain granules.

Formulation Example 6

| | |
|---|---|
| 2-Methyl-4-(pyridine-2-ylsulfonyl)trifluoro-methanesulfonanilide | 10 wt. parts |
| Xylene | 80 wt. parts |
| Calcium alkylbenzenesulfonate | 3 wt. parts |
| Polyoxyethylene sorbitan fatty acid ester | 7 wt. parts |

The components were mixed to obtain an emulsifiable concentrate.

Formulation Example 7

| | |
|---|---|
| Jeeklite | 78 wt. parts |
| Fine silicon dioxide | 15 wt. parts |
| Sodium naphthalene sulfonate-formaldehyde condensate | 2 wt. parts |
| Sulfate of a polyoxyethylene alkylaryl ether | 5 wt. parts |

The components were mixed and the mixture obtained was mixed with 2-trifluoromethyl-4-(pyridine-2-ylsulfonyl)methanesulfonanilide in a ratio of 4:1 by weight to obtain a wettable powder.

Formulation Example 8

| | |
|---|---|
| Sodium salt of 2-trifluoromethyl-4-(pyridine 2-ylsulfonyl)methanesulfonanilide | 20 wt. parts |
| Polyethyleneglycol octylphenyl ether | 5 wt. parts |
| Sodium dodecylbenzenesulfonate | 2 wt. parts |
| Water | 73 wt. parts |

The components were uniformly mixed to obtain a watermiscible solution.

What is claimed is:

1. A sulfonanilide compound having the formula (I):

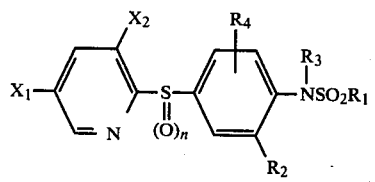

wherein $X_1$ is hydrogen atom, a halogen atom, methyl group or trifluoromethyl group, $X_2$ is hydrogen atom or a halogen atom, $R_1$ is a ($C_1$–$C_4$) alkyl group or a halo ($C_1$–$C_4$) alkyl group, $R_2$ is hydrogen atom, a ($C_1$–$C_4$) alkyl group, trifluoromethyl group or nitro group, $R_3$ is hydrogen atom, —$SO_2R_1$ group ($R_1$ is the same as defined above), a ($C_2$–$C_4$) acyl group, a ($C_2$–$C_4$) acylmethyl group, a ($C_1$–$C_4$) alkyl group, a ($C_1$–$C_4$) alkoxy ($C_1$–$C_4$) alkyl group or a ($C_3$–$C_4$) alkenyl group, $R_4$ is hydrogen atom or a halogen atom and n is an integer of 0 to 2; and a salt thereof.

2. The sulfonanilide compound according to claim 1, wherein the compound has the formula (II):

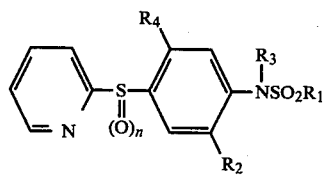

wherein $R_1$ is methyl group or trifluoromethyl group, $R_2$ is hydrogen atom or trifluoromethyl group, $R_3$ is hydrogen atom, methylsulfonyl group or acetyl group, $R_4$ is hydrogen atom or chlorine atom, and n is an integer of 0 to 2; and a salt thereof.

3. The compound according to claim 2, wherein $R_1$ is methyl group, $R_2$ is trifluoromethyl group, $R_3$ and $R_4$ are hydrogen atom, and n is an integer of 0 to 2.

4. The compound according to claim 2, wherein $R_1$ is trifluoromethyl group, $R_2$, $R_3$ and $R_4$ are hydrogen atom, and n is an integer of 0 to 2.

5. The compound according to claim 2, wherein $R_1$ is methyl group, $R_2$ is trifluoromethyl group, $R_3$ is hydrogen atom, $R_4$ is chlorine atom, and n is an integer of 0 to 2.

6. The compound according to claim 2, wherein $R_1$ is methyl group, $R_2$ is trifluoromethyl group, $R_3$ is acetyl group, $R_4$ is hydrogen atom, and n is an integer of 0 to 2.

7. The compound according to claim 2, wherein $R_1$ is methyl group, $R_2$ is trifluoromethyl group, $R_3$ is methylsulfonylgroup, $R_4$ is hydrogen atom, and n is an integer of 0 to 2.

8. The compound according to claim 1, wherein $X_1$, $X_2$, $R_2$, $R_3$ and $R_4$ are hydrogen atom, $R_1$ is trifluoromethyl group, and n is an integer of 0 to 2; and a salt thereof.

9. The compound according to claim 1, wherein $X_1$, and $X_2$ are respectively hydrogen atom or a halogen atom, $R_1$ is a ($C_1$–$C_4$) alkyl group or trifluoromethyl group, $R_2$ is hydrogen atom, a ($C_1$–$C_4$) alkyl group or trifluoromethyl group, $R_3$ is hydrogen atom or —$SO_2R_1$ group ($R_1$ is the same as defined above), $R_4$ is hydrogen atom, and n is an integer of 0 to 2; and a salt thereof, and $R_1$ is a ($C_1$–$C_4$) alkyl group when $X_1$, $X_2$, $R_2$, $R_3$ and $R_4$ are respectively hydrogen atom.

10. The compound according to claim 1, wherein the compound is 2-trifluoromethyl-4-(pyridine-2-ylthio) methanesulfonanilide.

11. The compound according to claim 1, wherein the compound is 2-trifluoromethyl-4-(pyridine-2-ylsulfinyl) methanesulfonanilide.

12. The compound according to claim 1, wherein the compound is 2-trifluoromethyl-4-(pyridine-2-ylsulfonyl) methanesulfonanilide.

13. The compound according to claim 1, wherein the compound is 4-(pyridine-2-ylthio) trifluoromethanesulfonanilide.

14. The compound according to claim 1, wherein the compound is 4-(pyridine-2-ylsulfinyl) trifluoromethanesulfonanilide.

15. The compound according to claim 1, wherein the compound is 4-(pyridine-2-ylsulfonyl) trifluoromethanesulfonanilide.

16. The compound according to claim 1, wherein the compound is N-methylsulfonyl-2-trifluoromethyl-4-(pyridine-2-ylthio) methanesulfonanilide.

17. The compound according to claim 1, wherein the compound is N-methylsulfonyl-2-trifluoromethyl-4-(pyridine-2-ylsulfinyl)methanesulfonanilide.

18. The compound according to claim 1, wherein the compound is N-methylsulfonyl-2-trifluoromethyl-4-(pyridine-2-ylsulfonyl)methanesulfonanilide.

19. A herbicidal composition comprising a herbicidally effective amount of a compound having the formula (I):

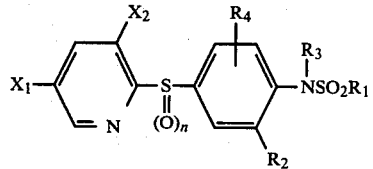

wherein $X_1$ is hydrogen atom, a halogen atom, methyl group or trifluoromethyl group, $X_2$ is hydrogen atom or a halogen atom, $R_1$ is a ($C_1$–$C_4$) alkyl group or a halo ($C_1$–$C_4$) alkyl group, $R_2$ is hydrogen atom, a ($C_1$–$C_4$) alkyl group, trifluoromethyl group or nitro group, $R_3$ is hydrogen atom, —$SO_2R_1$ group ($R_1$ is the same as defined above), a ($C_2$–$C_4$) acyl group, a ($C_2$–$C_4$) acylmethyl group, a ($C_1$–$C_4$) alkyl group, a ($C_1$–$C_4$) alkoxy ($C_1$–$C_4$) alkyl group or a ($C_3$–$C_4$) alkenyl group, $R_4$ is hydrogen atom or a halogen atom, and n is an integer of 0 to 2; and a salt thereof, as an active ingredient, and agriculturally acceptable adjuvants.

20. The herbicidal composition according to claim 19, wherein the compound has the formula (II):

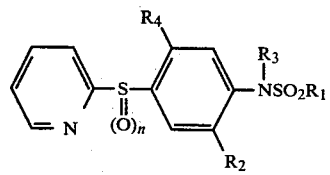

wherein $R_1$ is methyl group or trifluoromethyl group, $R_2$ is hydrogen atom or trifluoromethyl group, $R_3$ is hydrogen atom, methylsulfonyl group or acetyl group, $R_4$ is hydrogen atom or chlorine atom, and n is an integer of 0 to 2; and a salt thereof.

21. The herbicidal composition according to claim 20, wherein $R_1$ is methyl group, $R_2$ is trifluoromethyl group, $R_3$ and $R_4$ are hydrogen atom, and n is an integer of 0 to 2.

22. The herbicidal composition according to claim 20, wherein $R_1$ is trifluoromethyl group, $R_2$, $R_3$ and $R_4$ are hydrogen atom, and n is an integer of 0 to 2.

23. The herbicidal composition according to claim 20, wherein $R_1$ is methyl group, $R_2$ is trifluoromethyl group, $R_3$ is hydrogen atom, $R_4$ is chlorine atom, and n is an integer of 0 to 2.

24. The herbicidal composition according to claim 20, wherein $R_1$ is methyl group, $R_2$ is trifluoromethyl group, $R_3$ is acetyl group, $R_4$ is hydrogen atom, and n is an integer of 0 to 2.

25. The herbicidal composition according to claim 20, wherein $R_1$ is methyl group, $R_2$ is trifluoromethyl group, $R_3$ is methylsulfonyl group, $R_4$ is hydrogen atom, and n is an integer of 0 to 2.

26. The herbicidal composition according to claim 19, wherein $X_1$, $X_2$, $R_2$, $R_3$ and $R_4$ are hydrogen atom, $R_1$ is trifluoromethyl group, and n is an integer of 0 to 2; and a salt thereof.

27. The herbicidal composition according to claim 19, wherein $X_1$, and $X_2$ are respectively hydrogen atom or a halogen atom, $R_1$ is a ($C_1$-$C_4$) alkyl group or trifluoromethyl group, $R_2$ is hydrogen atom, a ($C_1$-$C_4$) alkyl group or trifluoromethyl group, $R_3$ is hydrogen atom or $-SO_2R_1$ group, $R_4$ is hydrogen atom, and n is an integer of 0 to 2; and a salt thereof, and $R_1$ is a ($C_1$-$C_4$) alkyl group when $X_1$, $X_2$, $R_2$, $R_3$ and $R_4$ are respectively hydrogen atom.

28. The herbicidal composition according to claim 19, wherein the compound is 2-trifluoromethyl-4-(pyridine-2-ylthio) methanesulfonanilide.

29. The herbicidal composition according to claim 19, wherein the compound is 2-trifluoromethyl-4-(pyridine-2-ylsulfinyl) methanesulfonanilide.

30. The herbicidal composition according to claim 19, wherein the compound is 2-trifluoromethyl-4-(pyridine-2-ylsulfonyl) methanesulfonanilide.

31. The herbicidal composition according to claim 19, wherein the compound is 4-(pyridine-2-ylthio) trifluoromethanesulfonanilide.

32. The herbicidal composition according to claim 19, wherein the compound is 4-(pyridine-2-ylsulfinyl) trifluoromethanesulfonanilide.

33. The herbicidal composition according to claim 19, wherein the compound is 4-(pyridine-2-ylsulfonyl) trifluoromethanesulfonanilide.

34. The herbicidal composition according to claim 19, wherein the compound is N-methylsulfonyl-2-trifluoromethyl-4-(pyridine-2-ylthio) methanesulfonanilide.

35. The herbicidal composition according to claim 19, wherein the compound is N-methylsulfonyl-2-trifluoromethyl-4-(pyridine-2-ylsulfinyl) methanesulfonanilide.

36. The herbicidal composition according to claim 19, wherein the compound is N-methylsulfonyl-2-trifluoromethyl-4-(pyridine-2-ylsulfonyl) methanesulfonanilide.

37. A method of controlling gramineous weeds, broad-leafed weeds and cyperaceae weeds in the presence of cultivated crops which comprises applying to the locus thereof a herbicidally effective amount of the herbicidal composition of claim 19.

* * * * *